(12) United States Patent
Carroll et al.

(10) Patent No.: US 8,432,549 B2
(45) Date of Patent: Apr. 30, 2013

(54) METHODS OF AND APPARATUS FOR DETERMINING PROPERTIES RELATING TO MULTI-PHASE SYSTEMS

(75) Inventors: John Carroll, Stockton on Tees (GB); Simon Robert Gibbon, Northallerton (GB)

(73) Assignee: Corn Products Development, Inc., Westchester, IL (US)

( * ) Notice: Subject to any disclaimer, the term of this patent is extended or adjusted under 35 U.S.C. 154(b) by 683 days.

(21) Appl. No.: 12/492,852

(22) Filed: Jun. 26, 2009

(65) Prior Publication Data

US 2010/0007891 A1    Jan. 14, 2010

(30) Foreign Application Priority Data

Jul. 8, 2008   (GB) .................................. 0812455.4

(51) Int. Cl.
*G01N 21/00*      (2006.01)
(52) U.S. Cl.
USPC .......................................... 356/432; 356/442
(58) Field of Classification Search .......... 356/432–436, 356/440–442, 444, 337–343, 244, 246, 73
See application file for complete search history.

(56) References Cited

U.S. PATENT DOCUMENTS

| | | | |
|---|---|---|---|
| 6,519,032 B1 | | 2/2003 | Kuebler et al. |
| 6,831,741 B1 * | | 12/2004 | De Kruif et al. ............... 356/338 |
| 7,227,622 B2 * | | 6/2007 | Itoh .................................. 356/39 |
| 7,339,668 B2 * | | 3/2008 | Ebersole et al. .............. 356/319 |
| 8,125,643 B2 * | | 2/2012 | Hansen et al. ................ 356/436 |
| 2003/0098969 A1 | | 5/2003 | Katz et al. |
| 2004/0265177 A1 | | 12/2004 | Nicoli et al. |
| 2005/0030541 A1 | | 2/2005 | Erlbacher et al. |

FOREIGN PATENT DOCUMENTS

EP    0947822    10/1999

OTHER PUBLICATIONS

Anonymous, "Product Catalogue 2004, Thermo Electron Corporation" [Online] 2004, pp. 18-27.
Nicoli, et al., Particle size analysis of colloidal suspensions by SPOS compared to DLS: A sensitive indicator of quality and stability; Jan. 2001, pp. 32,34,36,38-39; vol. 33, No. 1.

* cited by examiner

*Primary Examiner* — Tri T Ton
(74) *Attorney, Agent, or Firm* — Jones Day (57) ABSTRACT

A method of, and apparatus for, determining properties relating to multi-phase systems are provided. In the method, an array of sample tubes each containing a sample of a multi-phase system is formed. An iterative process is used to generate at least two data sets of transmitted and/or backscattered values for each sample and the data sets for each sample are processed to determine at least one property of the sample. The apparatus has a support on which an array of sample tubes each containing a sample of a multi-phase system may be assembled. It also has a wave source and at least one wave detector for detecting transmitted and/or backscattered values for each sample and computer means for iteratively operating said wave source and said at least one detector to generate data sets of transmitted and/or backscattered values for each sample and for processing the data sets for each sample to determine at least one property of the sample.

20 Claims, 12 Drawing Sheets

METHODS OF AND APPARATUS FOR DETERMINING PROPERTIES RELATING TO MULTI-PHASE SYSTEMS

CROSS REFERENCE TO RELATED APPLICATION

This application claims priority to provisional GB Application No. 0812455.4 filed Jul. 8, 2008, the entirety of which is incorporated herein by reference.

FIELD OF THE INVENTION

The present invention relates to methods of and apparatus for determining properties relating to multi-phase systems.

BACKGROUND OF THE INVENTION

It is of significant interest to determine the properties of multi-phase systems such as dispersions, emulsions and the like.

One example of a multi-phase system is that formed by hydrocolloids such as starch granules and rice grains swollen by water, particularly during a cooking process. The swell volumes of such systems are of particular interest as an aid to determining the potential suitability of particular starches in different applications, especially in the food industry. Currently, the swell volume is determined by cooking a predetermined quantity of starch granules in a known volume of water, placing the resultant multi-phase system in a laboratory measuring cylinder and allowing it to settle for 24 hours, following which the volume of the settled starch may be read from the cylinder. Clearly, the acquisition of data by this method is laborious and costly.

Another type of multi-phase system of interest, in the beverages industry, involves oil-in-water emulsions consisting inter alia of water, flavouring oils, stabilisers such as gum Arabic, colorants and other additives. As many beverages are required to have long shelf lives, it is important that any emulsion system used in such beverages is stable over a long period of time. Consequently, instabilities in the emulsion systems typically, unless unusually unstable, may take at least one month, if not longer, to become visually apparent to human observers of the systems. Such time frames to determine stability/instability of this type of emulsion system results in both the slow development of new emulsions and the slow identification of solutions to technical problems such as shear instability, raw material quality etc.

As will be well understood, there are many other applications in which the properties of multi-phase systems are of particular interest in which similar problems arise. It will be appreciated that, whilst in many applications the stability of such systems is of interest, in other applications the ability to destabilise such systems may be a primary aim.

It has been proposed in U.S. Pat. No. 5,783,826 to identify data from multi-phase systems using equipment consisting of a housing for a movable electromagnetic emitter and detector system and into which a cell containing a sample may be inserted and held vertically. The emitter/detector system is operable to measure backscattered radiation from the sample therein. If desired, radiation transmitted through the sample in the cell may also be acquired. By moving the emitter/detector system stepwise relative to the cell, a phase profile of the sample may be generated. Repetition of the cycle at time intervals may reveal changes in the phase profile indicative of instability in the sample. However, again this is time consuming and, if large numbers of multi-phase systems are to be examined, of high capital expenditure to provide sufficient numbers of equipment to deal with such numbers.

U.S. Pat. No. 6,466,319 discloses determining the stability of a liquid suspension by maintaining the particles therein uniformly suspended, for example by stirring, whilst immersing a measuring cell therein and determining the amount of backscatter generated by particles that have increased in size, for example by agglomerating or through some other aggregation mechanism.

U.S. Pat. No. 6,691,057 is similar to U.S. Pat. No. 5,783,826 except that it proposes irradiating the full length of the sample cell with the radiation to obtain a simultaneous scan of all points along the cell thereby avoiding errors generated by potentially rapid changes within the multi-phase system which may occur during a linear scan as proposed in U.S. Pat. No. 5,783,826. Additionally, U.S. Pat. No. 6,691,057 also discloses accelerating any settlement process in the cell by tilting the cell as an aid to gravitational settlement. The emitter/detector system is also tilted to maintain the orientation between it and the sample cell.

SUMMARY OF THE INVENTION

The present invention relates to methods of and apparatus for determining properties relating to multi-phase systems in which multiple samples are readily processed. Preferably, in such methods and apparatus, the properties of such multi-phase systems are determined relatively rapidly or, where the physical processes are slow such that the measurement takes considerable time, that the cost of such determinations can be minimised.

According to the present invention, a method of determining properties relating to multi-phase systems comprises:
 a) forming an array of sample tubes each containing a sample of a multi-phase system;
 b) in an iterative process, generating at least two data sets of transmitted and/or backscattered radiation values for each sample; and
 c) processing the data sets for each sample to determine at least one property of the sample.

The term "sample tube" as used in this specification is intended to cover any suitable receptacle for the samples which will permit radiation to be transmitted through or back scattered radiation received from the samples. Typically, the receptacle will conveniently comprise a sample tube having a circular or rectangular cross-section and will be made of a material having a high transmittance to the radiation used.

Preferably, the method according to the invention comprises storing the data sets.

Preferably, the method according to the invention comprises generating each data set by transmitting waves towards each tube and detecting transmitted and/or backscattered waves.

In a preferred embodiment, the method according to the invention comprises generating each data set by transmitting electromagnetic radiation towards each tube and detecting transmitted and/or backscattered radiation. Preferably, the electromagnetic radiation is in ultraviolet, visible or infrared and preferably has wavelengths in the range 100 μm to 10 nm typically 10 μm to 200 nm.

In an alternative embodiment, the method comprises transmitting acoustical waves towards each tube and detecting transmitted and/or backscattered acoustic waves.

In one embodiment, the method comprises subjecting substantially at least the whole of the axial extent of the sample to the waves at the same time detecting transmitted and/or backscattered waves as a line source to form a data set for the sample.

In a preferred embodiment, the method comprises moving a wave source axially relative to the tube to subject at least the whole of the axial extent of the sample therein sequentially to the waves and detecting transmitted and/or backscattered waves. Preferably, the method comprises moving the source continuously and generating the data set for each sample by sampling the detected transmitted and/or backscattered waves at timed intervals.

The timed intervals are selected to give a number of transmission measurements such that a meaningful plot of the transmission to sample height may be generated. Typically, for say a 20 second scan, at least 10 measurements should be recorded, more preferably at least 100 measurements and more particularly at least 400 measurements should be recorded. In a preferred embodiment, for a 20 second scan, at least 100 measurements, more preferably about 1000 measurements, should be recorded.

Thus, the timed intervals are selected to be between 0.001 seconds and 2 seconds, more preferably between 0.01 seconds and 0.1 second, and in particular between 0.01 seconds and 0.05 seconds. Typically, the timed intervals are 0.02 second during a 20 second scan, resulting in 1000 transmission measurements.

The time between complete scans typically can vary from 1 second to 1 month and, more preferably, 1 minute to 1 day for each sample.

In a preferred embodiment, the method comprises forming a fixed array of tubes. In a further preferred embodiment, the method comprises moving the wave source with respect to the tubes within the array. This has the advantage that the samples in the tubes in the array remain undisturbed during the whole of the test period.

In one embodiment of the invention, the method comprises moving a single wave source relative to each of the tubes to generate data sets therefrom.

In a preferred embodiment, the method comprises simultaneously moving at least two wave sources relative to at least two tubes in the array to simultaneously generate data sets therefrom.

Preferably, the method comprises forming the array by aligning the tubes to a common set of parallel axes.

In a preferred embodiment of the invention, this may be achieved by retaining each tube relative to two mutually-perpendicular reference surfaces, the first being vertical and in contact with a side wall of a respective tube and the second being horizontal and in contact with the base of the respective tube.

In a preferred embodiment, the method comprises providing a sampling initiation reference surface, detection of which during movement of the wave source axially relative to the tube initiates sampling of the detected transmitted and/or backscattered waves at said timed intervals.

In a particularly preferred embodiment, said sampling initiation reference surface comprises a third reference surface below and parallel to the horizontal surface. In this instance, said method comprises moving the wave source axially relative to the tube from below said third reference surface, monitoring the detected transmitted and/or backscattered waves to detect said third reference surface and initiating sampling of the detected transmitted and/or backscattered waves at said timed intervals when said third reference surface is detected.

By using a reference surface to initiate said sampling, variations in scans owing to minor differences in thicknesses of bases of tubes for example may be avoided. The distance between the second and third reference surfaces may also be used as a secondary distance calibration and check to ensure that the scanning system is functioning correctly.

The scan is normally terminated once a pre-determined distance has been covered by the source. In an alternative embodiment, which can be used with appropriate samples, the scan is terminated by monitoring the detected transmitted and/or backscattered waves and computationally determining when the top of the liquid has been reached.

In another preferred embodiment, the method comprises iteratively generating a first set of data for each tube in the array in sequence and then second and subsequent sets of data for each tube in sequence. Alternatively, the method may comprise iteratively generating a first set of data for each tube in a subset in the array in sequence and then second and subsequent sets of data for each tube in the subset in sequence and then repeating this process for second and subsequent subsets in the array.

In yet a further alternative, the method has sufficient flexibility to permit the sequence of scanning of arrays of tubes or sub-sets thereof to be be undertaken using a random programme; or to follow a sequence pre-determined by an operator prior to undertaking the measurements.

Additionally, the method may include the step of scheduling scans to achieve the largest number of appropriately timed scans for all the samples placed in the system. In another alternative, the method may include determining the sequence in which to carry out measurements based on the degree of change detected from previously generated data sets.

Preferably, the array may comprise at least two, more particularly at least twenty and especially at least one hundred tubes. Preferably, the array does not comprise more than one thousand, more particularly not more than five hundred tubes. Typically, the array may comprise two, three or four hundred tubes.

In the method of the invention, it is not necessary to place all the samples in the array at one time, but it is possible to add additional samples, until the sample capacity has been filled. It is also possible in full array at any time to replace samples for which no further information is required by new samples.

Also according to the present invention, apparatus for determining properties relating to multi-phase systems comprises a support on which an array of sample tubes each containing a sample of a multi-phase system may be assembled, a wave source and at least one wave detector for detecting transmitted and/or backscattered values for each sample and computer means for iteratively operating said wave source and said at least one detector to generate data sets of transmitted and/or backscattered values for each sample and for processing the data sets for each sample to determine at least one property of the sample.

Preferably, the computer means is capable of storing the data sets.

Preferably, the apparatus comprises a wave source capable of transmitting electromagnetic radiation and said at least one detector capable of detecting such radiation.

In an alternative embodiment, the apparatus comprises a wave source capable of transmitting acoustical waves and at least one detector capable of detecting such waves.

In one embodiment, the apparatus comprises a wave source capable of generating waves as a line source whereby substantially at least the whole of the axial extent of the sample may be subjected to the output therefrom, said at least one detector being capable of receiving transmitted and/or backscattered waves as a line source.

In a preferred embodiment, the apparatus comprises a wave source capable of generating waves as a point source, said at least one detector being capable of receiving transmitted and/or backscattered waves as a point source, said wave source and said at least one detector being movable as a unit axially relative to a tube to subject at least the whole of the axial extent of the sample therein sequentially to the radiation and to detect transmitted and/or backscattered waves.

Preferably, said computer is programmed to move the source continuously and to generate the data set for each sample by sampling the detected transmitted and/or backscattered waves at timed intervals.

The timed intervals are selected to give a number of transmission measurements such that a meaningful plot of the transmission to sample height may be generated. Typically, for say a 20 second scan, at least 10 measurements should be recorded, more preferably at least 100 measurements and more particularly at least 400 measurements should be recorded. In a preferred embodiment, for a 20 second scan, at least 100 measurements, more preferably about 1000 measurements, should be recorded.

Thus, the timed intervals are selected to be between 0.001 seconds and 2 seconds, more preferably between 0.01 seconds and 1 second, and in particular between 0.01 seconds and 0.05 seconds. Typically, the timed intervals are 0.02 second during a 20 second scan, resulting in 1000 transmission measurements.

Subsequent complete scans can be separated by times of between 1 second to 1 month and 1 minute to 1 day typically for each sample.

In a preferred embodiment, the support is not movable, at least during a data acquisition period, and the wave source is movable with respect to the support and hence to tubes supported thereby in an array. This has the advantage that the samples in the tubes in the array remain undisturbed during the whole of the test period.

In one embodiment of the invention, the apparatus comprises a single wave source which is movable relative to each of the tubes to generate data sets therefrom.

In a preferred embodiment, the apparatus comprises at least two wave sources each having an associated at least one detector, the at least two wave sources being movable relative to at least two tubes in the array to simultaneously generate data sets therefrom.

Preferably, said support on which an array of tubes may be assembled comprises, for each tube that is to form the array, a support means capable of aligning the tubes to a common set of parallel axes.

In a preferred embodiment of the invention, this may be achieved by a support means having two mutually-perpendicular reference surfaces, the first being vertical and contactable with a side wall of a respective tube and the second being horizontal and contactable with the base of the respective tube and retaining means for retaining a respective tube in contact with said surfaces.

In a preferred embodiment, the apparatus comprises a sampling initiation reference surface, detection of which during movement of the wave source axially relative to the tube initiates sampling of the detected transmitted and/or backscattered waves at said timed intervals.

In a particularly preferred embodiment, said sampling initiation reference surface comprises a third reference surface on said support means, said third reference surface being below and parallel to the second, horizontal surface. In this instance, said computer is programmed to move the wave source axially relative to a tube from a start position below said third reference surface and to monitor the detected transmitted and/or backscattered waves to detect said third reference surface and to initiate sampling of the detected transmitted and/or backscattered waves at said timed intervals following detection of said third reference surface.

In a preferred embodiment, said support means for each tube to form an array comprises a base from which two tube support members protrude substantially vertically. Said first reference surface is formed on one of said members and retaining means, preferably resilient retaining means, is carried on the other of said members such that a tube placed between said members is retained in contact with said first reference surface. Said upper and lower surfaces of the base comprise said second and third reference surfaces, said retaining means also functioning to retain the base of a tube in contact with said second reference surface.

As will be appreciated, the relationship between the surfaces is required to be formed with some accuracy to ensure repeatability and accuracy of results. Accordingly, it is preferred that the surfaces are machined surfaces. The machining of the surfaces may be mechanical machining or, preferably, the surfaces may be formed by laser cutting.

Preferably, the support means for a row of tubes in an array are integral with one another, i.e., the support means are formed on a common base from which protrudes pairs of support members; several such integrated support means being accurately assembled parallel and in horizontal and vertical alignment relative to one another to form the support on which the tubes may be assembled.

As discussed earlier in this specification, the method and apparatus of the invention has utility in many areas of application in which the stability or instability of multi-phase systems are of interest. Such systems include, but are not limiting to hydrocolloids in food applications, oil-in-water emulsions in the fields of beverages emulsion, oil-in-water emulsions in the fields of personal care and oil-field, etc.

DETAILED DESCRIPTION OF THE DRAWINGS

The invention is illustrated by reference to the following drawings.

DETAILED DESCRIPTION OF THE INVENTION

Figure 1:
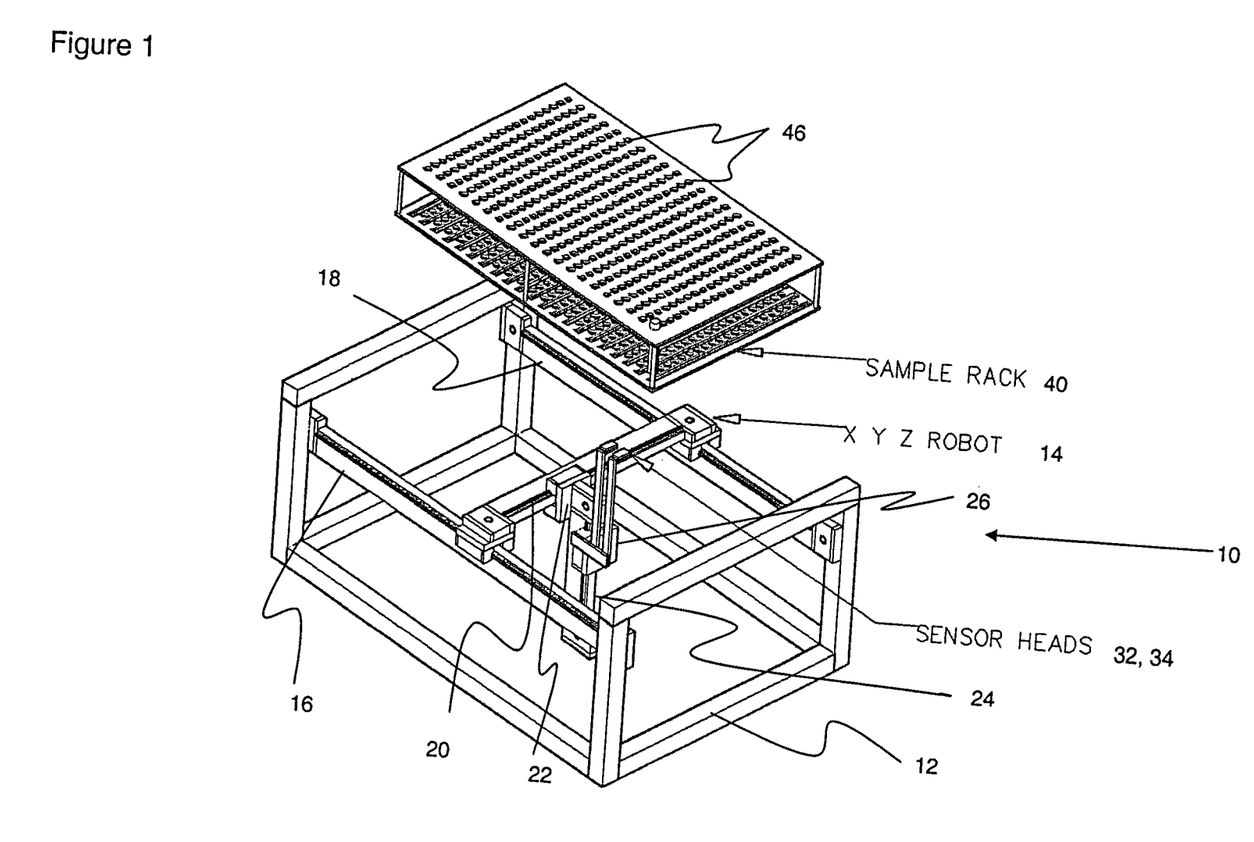
FIG. 1 is a perspective diagrammatic representation of part of apparatus according to the present invention.
Figure 2:
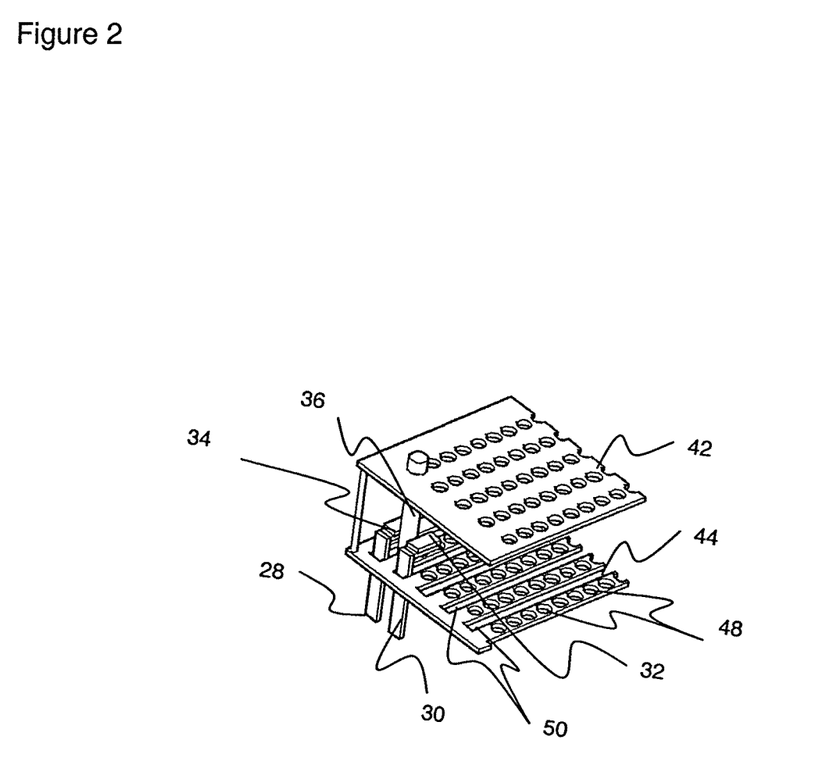
FIG. 2 is an enlarged perspective diagrammatic representation of part of the sample rack shown in FIG. 1 diagrammatically showing the scanning assembly located in a position partially through a scan of a sample tube located in the rack.

Referring to FIGS. 1 and 2, apparatus 10 according to the invention has a frame 12 on which is mounted an XYZ robot 14. The robot 14 has a pair of parallel rails 16, 18 mounted on opposite upper sides of the frame 12 to form a horizontal track on which an arm 20 is mounted for movement relative to the frame 12, say in the X direction. An assembly 22 is mounted on the arm 20 for movement along the arm 20 in the Y direction, the assembly 22 having depending therefrom a vertically-oriented arm 24. A scanning assembly 26 is mounted on the arm 24 for movement (in the Z direction) relative thereto, the scanning assembly 26 comprising two vertically-oriented parallel support members 28, 30 which respectively carry a radiation source 32 and a radiation detector 34.

The radiation source 32 is preferably a source of ultraviolet, visible or infrared radiation and may be a lamp, a light emitting diode ("LED") or a laser for example. Preferably, the source 32 is an LED capable of transmitting visible radiation. The detector 34 is capable of detecting transmitted or back-scattered ultraviolet, visible or infrared radiation depending upon the location of the detector 34 relative to the radiation source 32. In a preferred embodiment, the detector 34 is located opposite the source 32 to detect transmitted radiation. The detector 34 may be a photo-detector, eg a photodiode, a photomultiplier or a camera. Preferably, the detector 34 is a solid state photodiode capable of detecting visible radiation.

Motors (not shown) are provided to move the arm 20 along the track 16, 18; to move the assembly 22 along the arm 20; and to move the scanning assembly 26 along the arm 24. The motors are typically stepper motors operated in a continuous mode thus enabling the scanning assembly 26 to be located very accurately relative to the frame 12 and hence to sample tubes 36 carried by a sample rack 40 locatable on the frame 12 (shown above the frame 12 in FIG. 1 for clarity).

The sample rack 40 has upper and lower vertically spaced-apart plates 42, 44 each having an array of four hundred holes 46, 48, the arrays of holes 46, 48 being aligned with one another whereby pairs of holes 46, 48 each have a common vertical axis. Accordingly, sample tubes 36 located in each pair of holes 46, 48 are all aligned to a common set of parallel axes.

The peripheries of the holes 46, 48 form first and second reference surfaces which locate the sample tubes 36 such that their longitudinal axes are essentially vertical. The holes 46 in the upper plate 42 are sized such that the sample tubes 36 are close fits in the holes 46 whereas the holes 48 in the lower plate 44 may be slightly smaller than the holes 46 and act to locate the base of the tubes 36 relative to the lower plate 44. In an alternative embodiment, the holes 48 in the lower plate 44 may be the same size as the holes 46 but they do not extend completely through the lower plate 44.

The lower plate 44 of the sample rack 40 is also provided with parallel slots 50 between each row of holes 46 and next to each end row of holes 46 whereby each row of holes 46 is bracketed by a pair of adjacent slots 50. The slots 50 are each slightly longer than the extent of the rows of holes 46. The slots 50 permit the support members 28, 30, and hence the radiation source 32 and the detector 34, of the scanning assembly 26 to pass through pairs of adjacent slots 50 such that the source 32 and the detector 34 are on opposite sides of the sample tubes 36 in a specific row and are able to traverse vertically the full axial lengths of the tubes 36 (see FIG. 2).

A computer 52 (see FIG. 3), which is loaded with suitable control and processing software and has a visual display screen 54, is provided to control operation of the apparatus 10.

Typically, the apparatus 10 is operated as follows.

The sample rack 40 is loaded, either partially or fully, with sample tubes 36 containing multi-phase systems to be examined. The sample tubes 36 may be loaded into the rack 40 either manually or using automated tube handling equipment (not shown). During loading, the rack 40 may be either located on the frame 12 of the apparatus 10 or it may be located remotely from the frame 12 to which it introduced either manually or using automated rack handling equipment (not shown) once the sample tubes 36 are loaded into it.

As many multi-phase systems may start to separate relatively rapidly, in a preferred embodiment the rack 40 is located on the frame 12 during loading of the sample tubes 36 therein. This enables the computer 52 to schedule initial scanning of the sample tubes 36 within appropriate time frames for the multi-phase samples under consideration.

The computer 52 controls the motors of the robot 14 to position the scanning assembly 26 beneath a first sample tube 36 and then moves the assembly 26 vertically such that the radiation source 32 and the detector 34 pass through a pair of adjacent slots 50 on either side of the tube 36 to scan the contents of the tube 36 as is explained in more detail below with reference to FIGS. 3 to 7.

Figure 3:
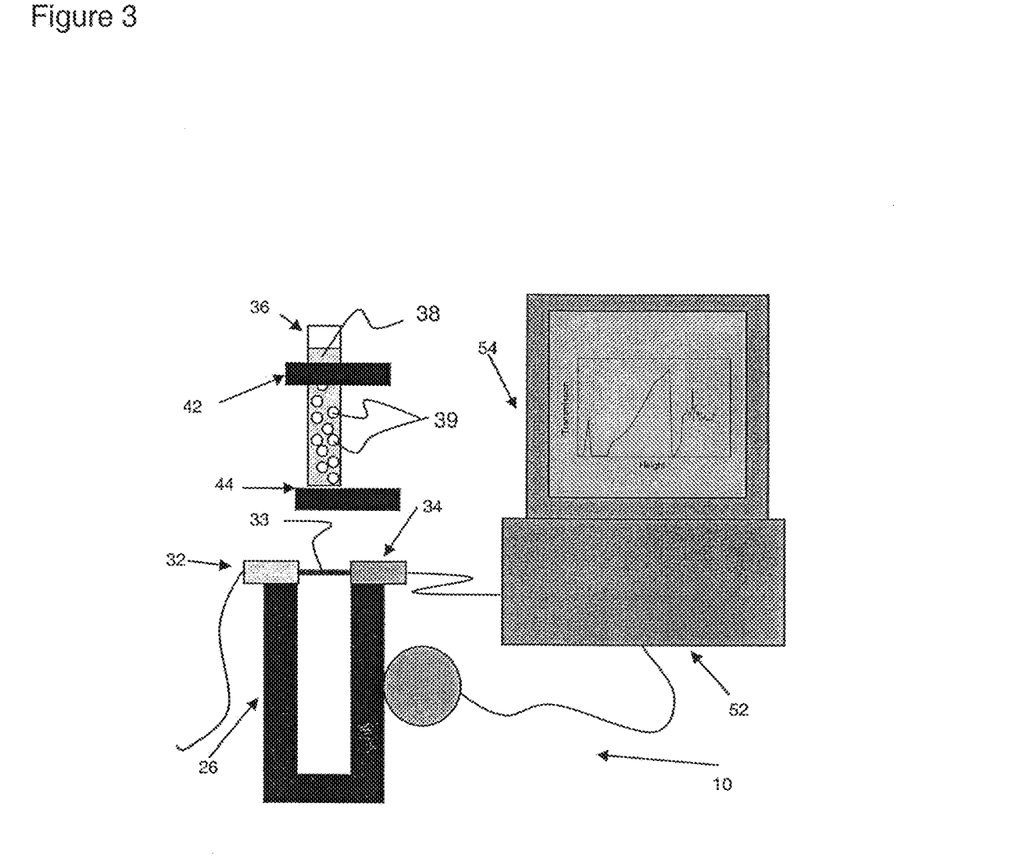
FIG. 3 is a diagrammatic representation of a complete system with only a single sample position demonstrated.

Referring now to FIG. 3, at the single sample position, the plates 42, 44 of the sample rack 40 support a sample tube 36 in a vertical position as described earlier. The sample tube 36 is shown filled with liquid 38 in which are dispersed particles of material 39, for example cooked starch particles. The particles 39 have partially settled.

As previously described, the scanning assembly 26 has an LED 32 for generating a light beam 33 and a photodiode 34 for detecting transmitted light.

Figure 4:
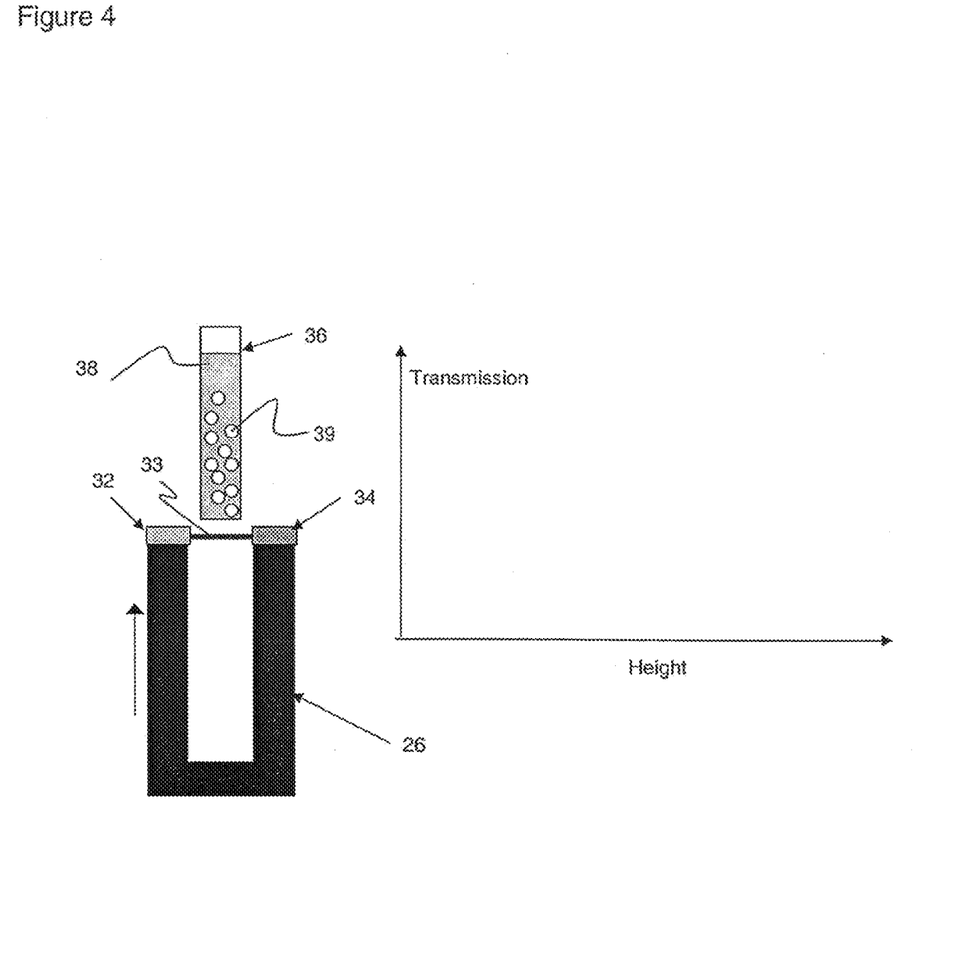
FIGS. 4 to 7 diagrammatically show the scanning assembly and sample tube shown in FIG. 3 in different positions relative to one another to demonstrate the sequence of movement of the scanning assembly necessary to develop and display as a graph a transmission profile of a sample in the sample tube.

Referring to FIG. 4, the LED 32 is shown held located within the scanning assembly 26, pointing towards the photodiode 34. The LED 32 and the photodiode 34 are aligned such that their primary axes are collinear. The assembly 26 is shown in its standby location, with the sample tube 36 fixed in position above the assembly 26. The graph on the display 54 is not registering any transmission as, when the assembly 26 is in this standby position, the computer 52 is not acquiring any data and, consequently, does not record transmission.

Figure 5:
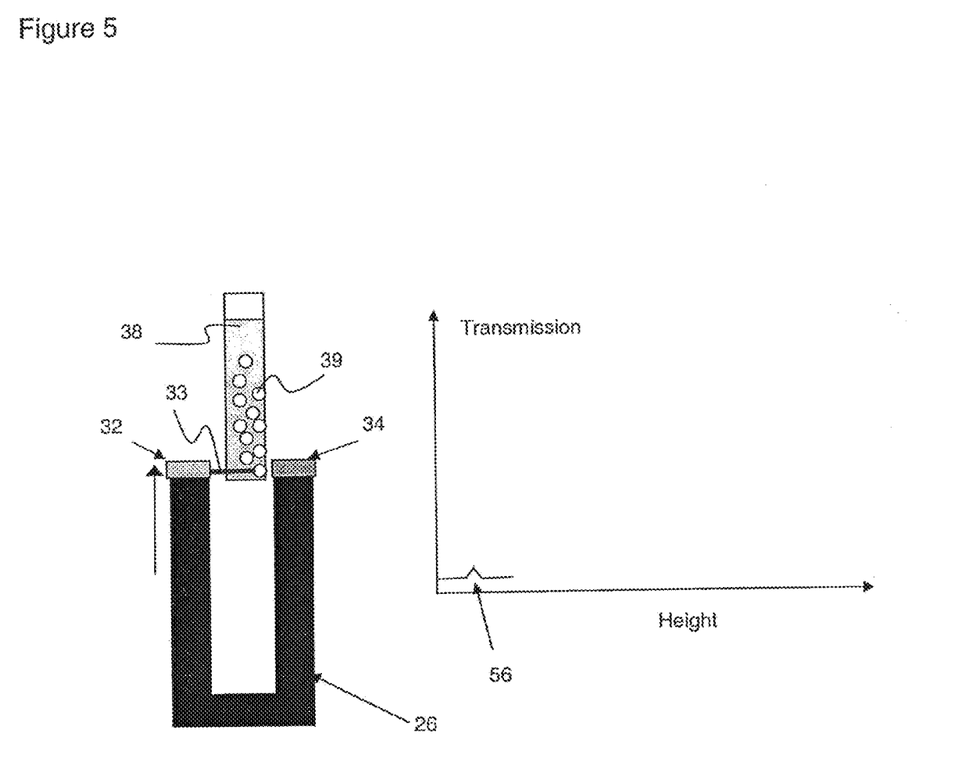

In FIG. 5, scanning process has been initiated, the scanning assembly 26 having been moved from its standby position shown in FIG. 4 vertically past the lower surface of the lower plate 44 of the sample rack 40 up to a position in which the LED 32 and the photodiode 34 are on opposite sides of the sample tube 36. As the LED 32 and the photodiode 34 pass the lower surface of the plate 44, the light beam is interrupted. This interruption is used as a reference for the computer 52 to start to record the transmission signal received by the photodiode 34 and to show it on the graph shown on the display 54. As the LED 32 and the photodiode 34 pass the plate 44, the transmission is essentially zero. The photodiode 34 then registers a transmission bump 56 followed by low/nearly zero transmission as most of the light is stopped by the particles 39 dispersed at this height in the sample tube 36.

Figure 6:
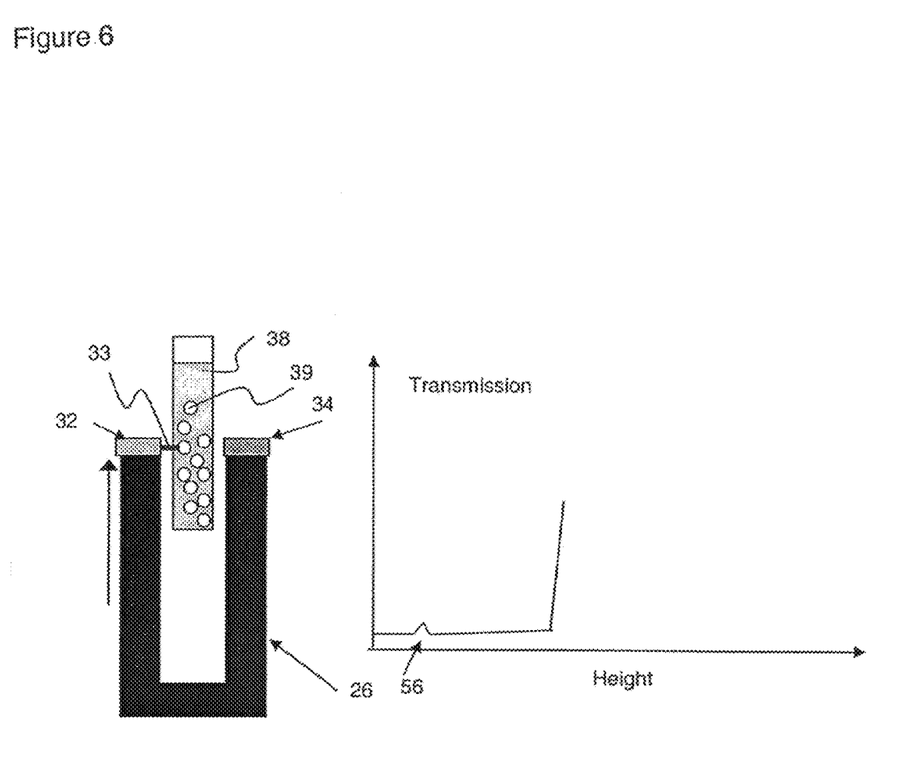

As the scanning assembly 26 moves up vertically relative to the sample tube 36, see FIG. 6, the number of particles intercepting the light beam reduces and transmission of the light beam 33 by the photodiode 34 is detected and recorded.

Figure 7:
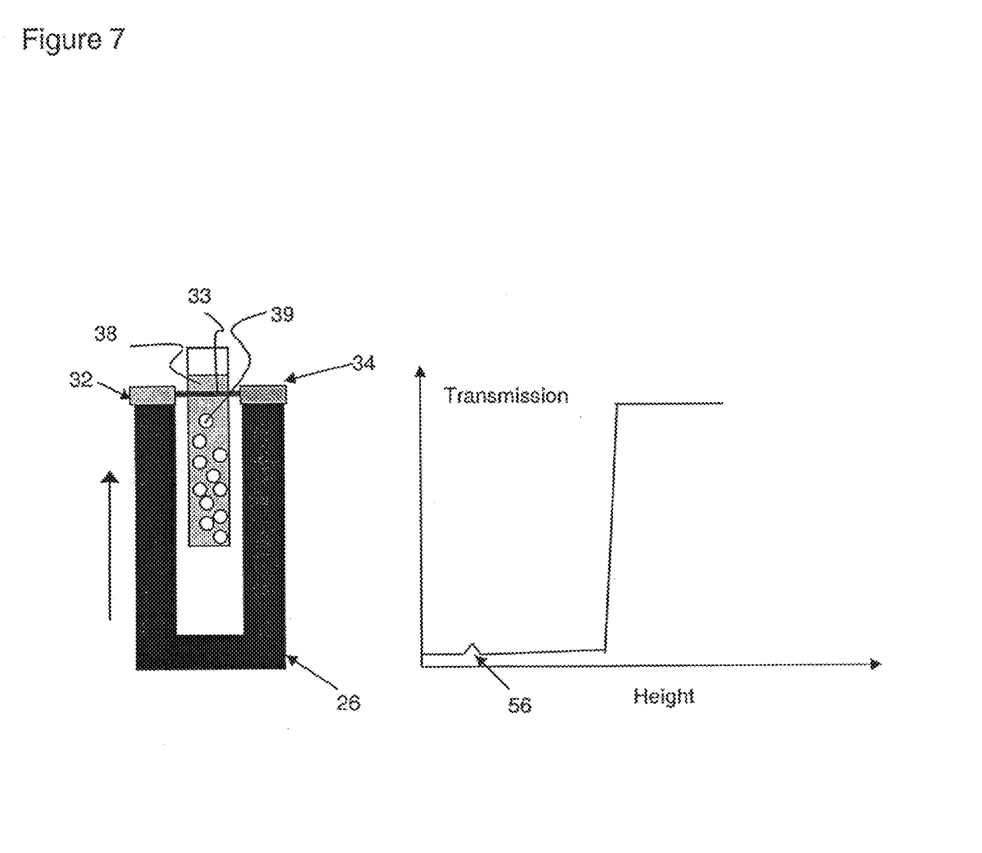

As the scanning assembly 26 moves even further up the tube 36, see FIG. 7, the liquid 38 in the sample tube 36 is essentially particle free and, consequently, the level of transmission of the light beam received by the photodiode 34 is high and the graph levels off.

Figure 8:
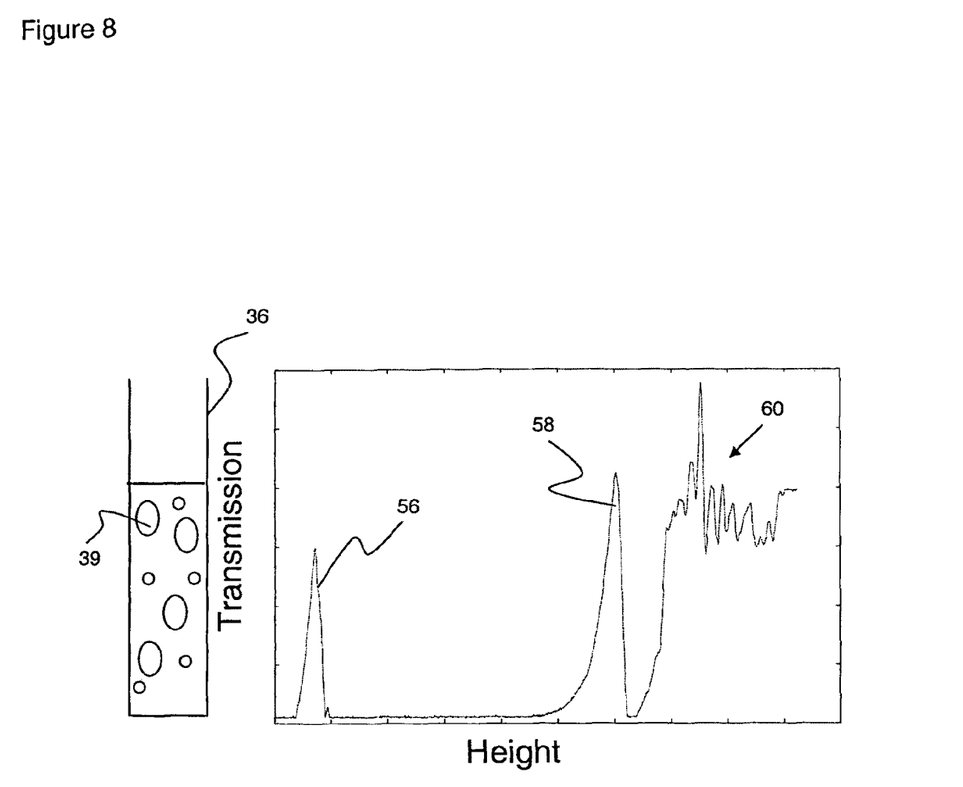
FIGS. 8 to 10 show a diagrammatic representation of a sample tube containing a cooked starch sample when just mixed, partially settled and fully settled, respectively, together with the transmission graphs generated by sequential scans of the tube at each stage.
Figure 9:
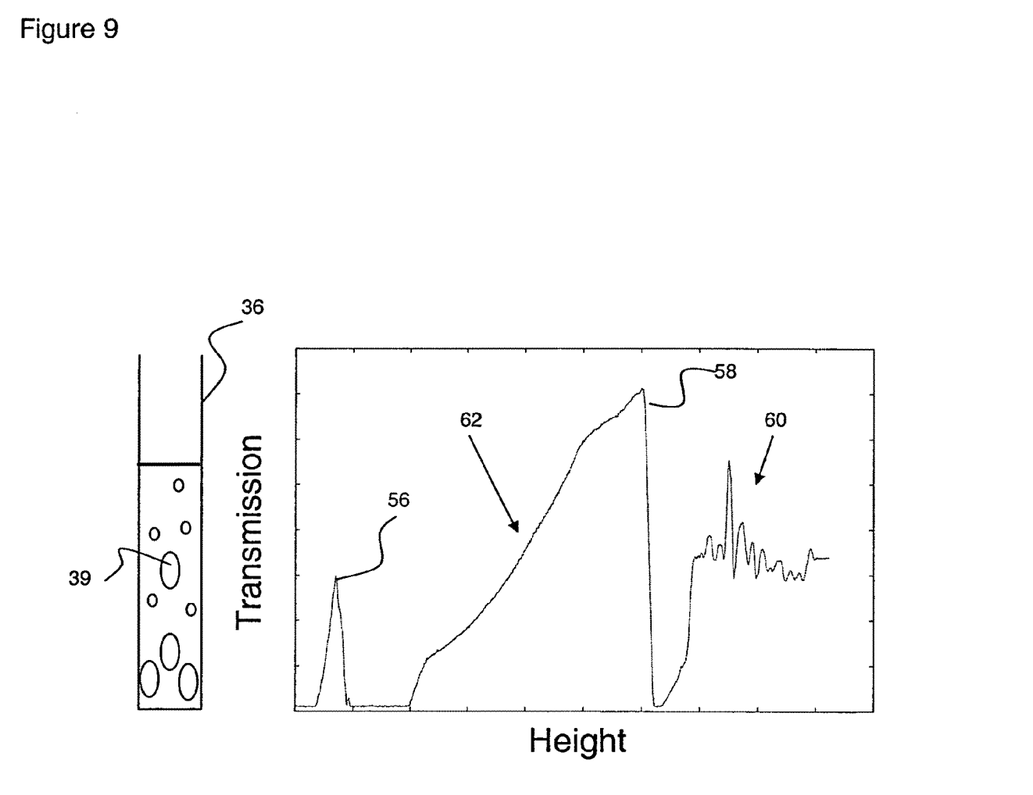
Figure 10:
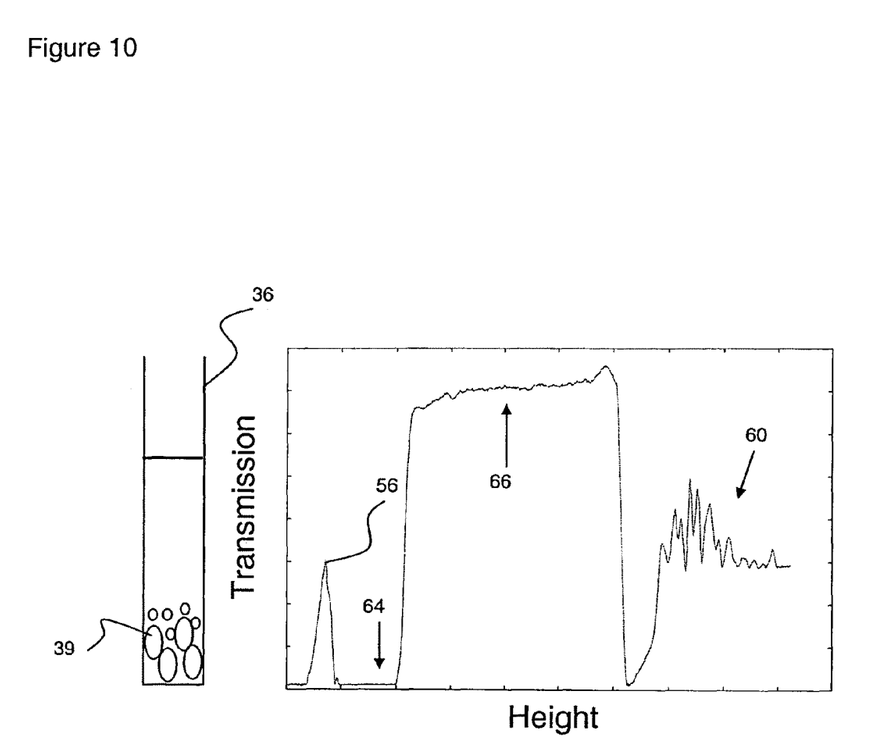

Reference is now made to FIGS. 8 to 10.

As shown in FIG. 8, in the well-mixed starch dispersion at time zero after mixing, the starch particles 39 are dispersed throughout the liquid in the sample tube 36. The transmission plot obtained when the tube 36 is scanned has a number of features. The transmission is essentially zero as the LED 32 and the photodiode 34 pass the plate 44 until a peak 56 in transmission occurs as they pass the clear glass base of the sample tube 36. This peak 56 is followed by a region of very low transmission where the light has been blocked by the dispersed starch particles. A transmission peak 58 then occurs due to light piping at the liquid-air interface. Finally, a noisy relatively high transmission area 60 is seen where the light beam goes through dirt and condensation above the liquid interface-air interface.

In FIG. 9, the starch particles 39 have settled for a short length of time with the consequence that some of the larger starch particles 39 have fully settled, but settling is still progressing. In the transmission plot obtained when the sample tube 36 is scanned, the same basic features are seen as were described for FIG. 8. However, the significant difference is that the transmission which corresponds to the starch dispersion now shows a region 62 of increasing transmission as the scanning assembly 26 moves vertically relative to the tube 36, the increasing transmission reflecting the gradual settling of the starch particles, falling from the top of the tube 36 down to the bottom.

In FIG. 10, the starch particles 39 have been allowed to completely settle, with all the starch particles 39 now packed at the bottom of the sample tube 36. In the transmission plot obtained when the sample tube 36 is scanned, the same basic features are seen as were described for FIG. 8. However, the plot now shows two distinct regions, a low transmission region 64 corresponding to the packed starch particles and a high transmission region 66 corresponding to the clear supernatant liquid left above the starch particles 39.

The behaviour of multi-phase systems may be examined using the method and apparatus of the invention as follows.

Stable emulsions: a stable emulsion is present if there is little change in successive transmission plots.

Unstable emulsions: an unstable emulsion is present if the multi-phase system exhibits sedimentation, creaming, separation into multiple layers or fading.

When sedimentation occurs, the plot exhibits an area of little or zero transmission near the bottom of the sample tube where the sediment is collecting and successive plots show an increase in transmission in the region of the sample tube above that where the sediment is accumulating. It is possible to derive sediment height and, therefore, volume from such data if required.

Creaming is the opposite of sedimentation in that the particles, for example oil droplets in an oil-in-water emulsion, rise to the top of the liquid in the sample tube. In this instance, successive transmission plots show an increase in transmission in the lower region of the tube and either little change or a decrease in transmission in the upper region of the tube.

Separation into multiple layers may occur in systems in which for example some fine particles are present. Thus, larger particles may sediment and the finer particles remain in suspension but tend to accumulate in a band. Such a band is apparent from successive transmission plots owing to the appearance and growth of a spike of reduced transmission in a region of the tube different to that in which the sediment is accumulating.

Fading is detectable by a gradual increase in transmission over the length of the tube with time.

Figure 11:
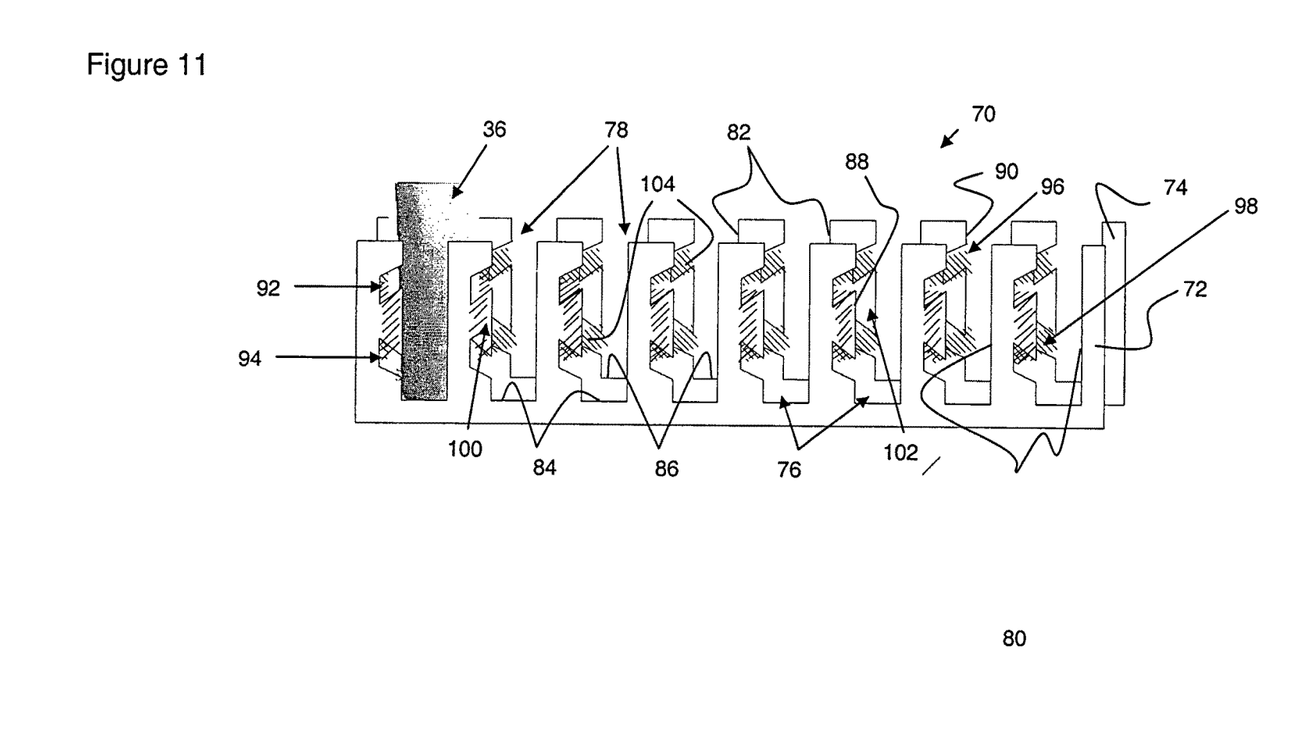
FIG. 11 is a diagrammatic representation of part of a preferred embodiment of a sample rack used in apparatus according to the invention.

Referring to FIG. 11, a preferred embodiment of a sample rack will now be described.

A sample rack 70 has pairs of vertically-oriented plates 72, 74 (only one pair shown). The plates 72, 74 in each pair are accurately held in spaced, parallel relationship to one another by suitable fixing means such as bolts and spacer tubes (not shown). Each pair of plates 72, 74 is clamped at its ends in clamping assemblies (not shown) carried by horizontally-oriented, parallel support bars (not shown) by which the rack 70 is mountable on the frame 12 of the apparatus. The pairs of plates 72, 74 are mounted spaced apart from adjacent pairs of plates 72, 74 whereby the LED 32 and photodiode 34 of the scanning assembly 26 may move vertically upward on opposite sides of the pairs of plates 72, 74.

Each pair of plates 72, 74 is provided with a plurality, eg eight, of vertically-oriented slots 76 and 78, respectively, the slots 76 in each plate 72 being in alignment with the slots 78 in each plate 74. The slots 76, 78 are accurately machined into the plates 72, 74 to provide first, vertically-oriented reference surfaces 80, 82, respectively, on one side of the slots 76, 78 and second, horizontally-oriented reference surfaces 84, 86 forming the bases of the slots 76, 78, respectively. The reference surfaces 80, 82 and 84, 86 are perpendicular to one another.

The opposite, vertically-oriented walls 88, 90 of the slots 76, 78, respectively, are each provided with a pair of recesses 92, 94 and 96, 98 respectively. In each pair of recesses 92, 94 and 96, 98, the recesses are at an acute but opposite angle to a horizontal axis passing between them to form isosceles trapezoidal shaped portions 100, 102 in the plates 72, 74. Resilient members 104, such as springs with their ends joined together to form a loop, are each located under tension in the aligned pairs of recesses 92, 94 and 96, 98 in each pair of plates 72, 74.

The dimensions of the slots 76, 78 and the spacing between the plates 72, 74 in each pair thereof are such that, in use, sample tubes 36 (only one shown) may be located in the pockets defined by adjacent pairs of slots 76, 78 in each pair of plates 72, 74, the resilient members 104 being used to press the sample tubes 36 into contact with the vertically-oriented reference surfaces 80, 82. The sample tubes 36 are pushed down until the bases of the tubes contact the horizontally-oriented reference surfaces 84, 86, ie the bases of the slots 76, 78. Thus, the sample tubes 36 are held in predetermined positions relative to the pair of plates 72, 74 in which they are located with their longitudinal axes held vertically.

This is particularly important when using circular cross-section sample tubes 36 as it is important that the light beam enters and exits the sample tube 36 perpendicular to its surface. That requires the light beam to accurately transverse the vertical centre line of the sample tube 36. It is preferable that, for circular cross-section sample tubes 36, no other actuation is required and, consequently, accurately machined reference surfaces 80, 82 and 84, 86 as described in this embodiment enable the light beam to traverse the centre lines of the sample tubes 36.

Figure 12:
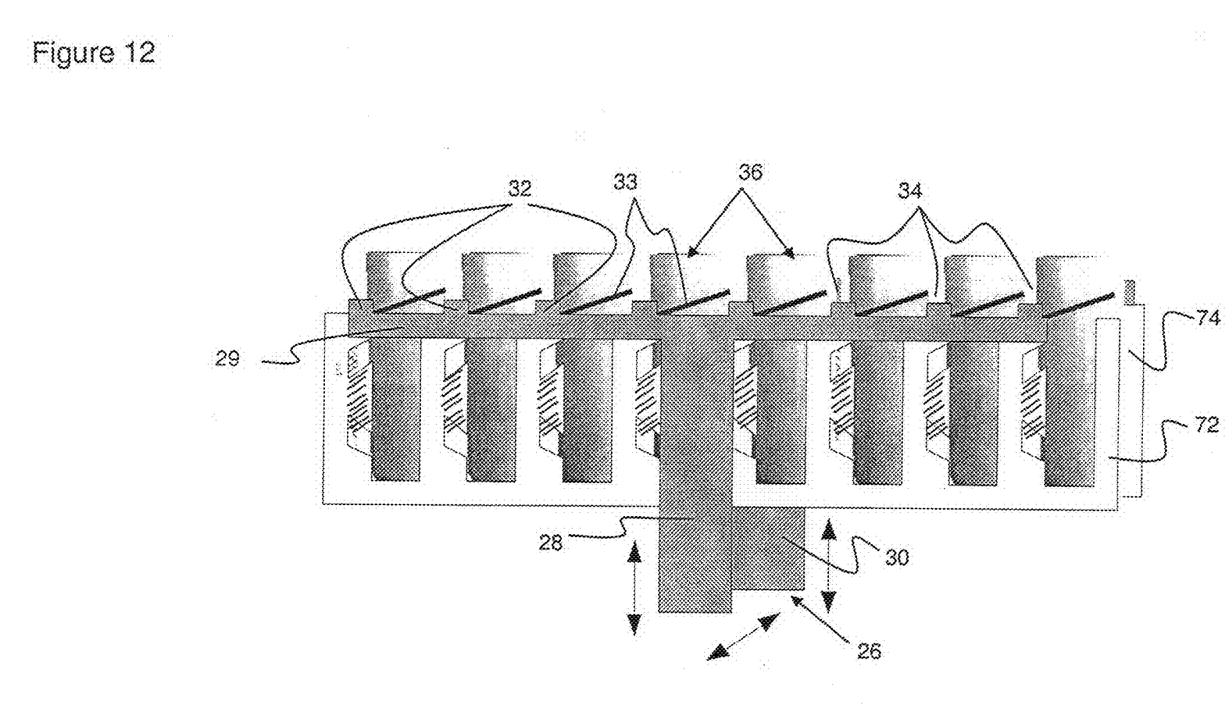
FIG. 12 is a diagrammatic representation similar to FIG. 11, but showing multiple radiation sources and detectors.

In particular, this also enables the use of multiple LEDs 32 with corresponding photodiodes 34 to scan rows of samples tubes together in one pass as is shown in FIG. 12. As shown in FIG. 12, for a row of eight sample tubes 36, the scanning assembly 26 has eight LEDs 32 mounted on a horizontal arm 29 fixed on the upper end of the support member 28. A corresponding arm (not shown) is fixed to the upper end of the support member 30 and has eight photodiodes 34 mounted thereon. This arrangement permits the row of eight samples in the sample tubes 36 to be analysed simultaneously. The signals from the multiple photodiodes 34 are acquired simultaneously in parallel by the signal processing system, for example using a single multi-channel analogue-to-digital converter card loaded into the computer 52.

As will be apparent, in this embodiment of the apparatus using a multiple source/detector arrangement means that, if desired, the robot 14 may be simplified to an XZ robot.

In an alternative embodiment (not shown), if it is not possible or it is too expensive to obtain accurately-machined parts for the apparatus of the invention or the circular cross-section sample tubes are not of good quality, ie they are not identically sized, then each detector/source may be provided with a fine actuation mechanism which moves them independently to the centre line of the sample tubes which may be determined by an initialisation scan across the widths of the sample tubes. A preferred form of actuation mechanism is a piezo actuation mechanism wherein an applied voltage causes at least one dimension change in a piezo crystal. Such a mechanism permits very small, accurate positioning adjustments to be made.

In the following claims, "comprising" or "comprises" is intended to mean "including the following elements but not excluding others"; "consisting of" or "consists of" is intended to mean "excluding more than trace amounts of other than the recited elements"; and "consisting essentially of" is intended to mean "excluding other elements of any essential significance to the claimed combination."

What is claimed is:

1. A method of determining properties relating to multi-phase systems comprising:
    a) introducing at least one multi-phase sample into a sample tube, having a longitudinal axis, contained within a sample tube array loaded in a sample rack, wherein the sample rack comprises:
        i) an upper plate comprising at least one series of holes, wherein each hole is suitable for receiving a sample tube; and
        ii) a lower plate, vertically spaced-apart from the upper plate, comprising:
            1) at least one series of holes vertically-aligned with the at least one series of holes in said upper plate, wherein each hole is suitable for receiving a sample tube; and
            2) at least one slot arranged alongside the at least one series of holes in said lower plate;
    b) generating at least a first and second data set by passing a transmitting wave source, a detector, or both, through the at least one slot positioned alongside the sample tube having the at least one multi-phase sample, said at least first and second data set comprising transmitted values, backscattered values, or both, for at least a first portion and at least a second portion of the at least one multi-phase sample, respectively, wherein the at least first and second portions differ at least, in part, with respect to the at least one multi-phase sample; and
    c) processing the at least first and second generated data sets for the at least one multi-phase sample to determine one or more properties of said at least one multi-phase sample.

2. The method of claim 1, wherein the at least first and second data sets are generated sequentially.

3. The method of claim 1, wherein the at least first and second portions differ at least, in part, with respect to the longitudinal axis of the sample tube.

4. The method of claim 1, wherein the sample tube containing the at least one multi-phase sample is positioned proximate to a transmitting wave source, a detector, or both.

5. The method of claim 4, wherein the proximate position is parallel or adjacent to the longitudinal axis of said sample tube containing the at least one multi-phase system sample.

6. The method of claim 4, wherein the generating the at least first data set, the at least second data set, or both, further comprises moving the transmitting wave source, the detector, or both, adjacent to the longitudinal axis of the sample tube containing the at least one multi-phase sample.

7. The method of claim 4, wherein the generating the at least first data set, the at least second data set, or both, further comprises moving the transmitting wave source, the detector, or both, parallel to the longitudinal axis of the sample tube containing the at least one multi-phase sample.

8. The method of claim 4, wherein the generating the at least first data set, the at least second data set, or both, further comprises moving the sample tube containing the at least one multi-phase sample along the longitudinal axis of said at least one sample tube.

9. The method of claim 4, wherein the generating the at least first data set, the at least second data set, or both, further comprises moving the sample tube containing the at least one multi-phase sample adjacent to either the transmitting wave source, the detector, or both.

10. The method of claim 4, wherein the wave source transmits electromagnetic radiation towards the sample tube, and the detector detects transmitted radiation, backscattered radiation, or both.

11. The method of claim 4, wherein the sample tube array comprises a fixed array of sample tubes, and wherein the wave source moves with respect to the sample tubes within said sample tube array.

12. The method of claim 1, wherein the sample tube array comprises at least a first sample tube containing a first multi-phase sample and at least a second sample tube containing a second multi-phase sample.

13. The method of claim 12, comprising generating:
    i) at least a first and second data set comprising transmitted values, backscattered values, or both, for at least a first portion and at least a second portion of the at least the first multi-phase sample, respectively; and
    ii) at least a first and second data set comprising transmitted values, backscattered values, or both, for at least a first portion and at least a second portion of the at least the second multi-phase sample, respectively.

14. The method of claim 13, wherein the at least a first and second data sets of the at least first multi-phase sample and the at least second multi-phase sample, respectively, are generated substantially simultaneously.

15. The method of claim 13, wherein the at least a first and second data sets of the at least first multi-phase sample and the at least second multi-phase sample, are generated by moving at least a first wave source and at least a second wave source relative to the longitudinal axis of said at least first multi-phase sample and said at least second multi-phase sample, respectively.

16. The method of claim 1, comprising forming the array by retaining each tube relative to two mutually-perpendicular reference surfaces, the first being vertical and in contact with a side wall of a respective tube and the second being horizontal and in contact with the base of the respective tube.

17. A method of determining properties relating to multi-phase systems comprising:
    a) introducing at least one multi-phase sample into a sample tube, having a longitudinal axis, contained within a sample tube array loaded in a sample rack, wherein the sample rack comprises:
        i) an upper plate comprising at least one series of holes, wherein each hole is suitable for receiving a sample tube; and
        ii) a lower plate, vertically spaced-apart from the upper plate, comprising:

1) at least one series of holes vertically-aligned with the at least one series of holes in said upper plate, wherein each hole is suitable for receiving a sample tube; and
2) at least one slot arranged alongside the at least one series of holes in said lower plate;

b) generating a series of data sets by passing a transmitting wave source, a detector, or both, through the at least one slot positioned alongside the sample tube having the at least one multi-phase sample, said series data sets comprising transmitted values, backscattered values, or both, for a series of portions of the at least one multi-phase sample, respectively, wherein the series of portions differ at least, in part, with respect to the at least one multi-phase sample; and c) processing the series of generated data sets for the at least one multi-phase sample to determine one or more properties of said at least one multi-phase sample.

18. The method of claim 17, wherein the series of portions differ at least, in part, with respect to the longitudinal axis of the sample tube.

19. The method of claim 17, wherein the sample tube containing the at least one multi-phase sample is positioned proximate to a transmitting wave source, a detector, or both.

20. An apparatus for determining at least one property relating to multi-phase systems, comprising:

a) a sample tube array, comprising one or more sample tubes, each sample tube having a longitudinal axis and each suitable for receiving a multi-phase sample;

b) a sample rack, comprising:
  i) an upper plate, comprising at least one series of holes, wherein each hole is suitable for receiving a sample tube; and
  ii) a lower plate, vertically spaced-apart from the upper plate, comprising:
    1) at least one series of holes vertically-aligned with the at least one series of holes in said upper plate, wherein each hole is suitable for receiving a sample tube; and
    2) at least one slot arranged alongside the at least one series of holes in said lower plate; and c) scanning system, comprising a computer, said computer is suitable for:
  i) controlling one or more wave sources;
  ii) controlling one or more wave detectors to generate at least a first and second data set comprising transmitted values, backscattered values, or both, for at least a first portion and at least a second portion of each of the multi-phase samples in the one or more sample tubes, respectively, wherein the at least first and second portions differ at least, in part, with respect to the one or more multi-phase samples; and
  iii) processing the generated data sets for each of the multi-phase samples to determine the at least one property of said multi-phase samples.

* * * * *